United States Patent
Busch

(10) Patent No.: US 10,010,649 B2
(45) Date of Patent: Jul. 3, 2018

(54) METHOD AND MEANS FOR CULTURING OSTEOBLASTIC CELLS

(75) Inventor: Christer Busch, Uppsala (SE)

(73) Assignee: Ascendia AB, Kista (SE)

( * ) Notice: Subject to any disclaimer, the term of this patent is extended or adjusted under 35 U.S.C. 154(b) by 1372 days.

(21) Appl. No.: 12/598,811

(22) PCT Filed: May 2, 2008

(86) PCT No.: PCT/SE2008/000307
§ 371 (c)(1),
(2), (4) Date: Dec. 3, 2009

(87) PCT Pub. No.: WO2008/136733
PCT Pub. Date: Nov. 13, 2008

(65) Prior Publication Data
US 2010/0080836 A1      Apr. 1, 2010

(30) Foreign Application Priority Data

May 4, 2007   (SE) ...................................... 0701078

(51) Int. Cl.
*A61L 27/20*   (2006.01)
*A61L 27/38*   (2006.01)
*C12N 5/077*   (2010.01)
*C12N 5/0775*  (2010.01)

(52) U.S. Cl.
CPC ........... *A61L 27/20* (2013.01); *A61L 27/3821* (2013.01); *A61L 27/3834* (2013.01); *A61L 27/3847* (2013.01); *A61L 27/3865* (2013.01); *A61L 27/3895* (2013.01); *C12N 5/0654* (2013.01); *C12N 5/0663* (2013.01); *A61L 2430/02* (2013.01); *C12N 2533/78* (2013.01)

(58) Field of Classification Search
CPC .. A61L 27/20; A61L 2430/02; A61L 27/3821; A61L 27/3834; C08L 1/08
USPC ........................................................ 435/395
See application file for complete search history.

(56) References Cited

U.S. PATENT DOCUMENTS

| | | | |
|---|---|---|---|
| 4,228,227 A * | 10/1980 | Saathoff et al. | 429/337 |
| 5,717,006 A * | 2/1998 | Daculsi et al. | 523/115 |
| 6,001,394 A * | 12/1999 | Daculsi et al. | 424/489 |
| 2003/0220696 A1 | 11/2003 | Levine et al. | |
| 2005/0271740 A1* | 12/2005 | Lin et al. | 424/602 |
| 2007/0212389 A1* | 9/2007 | Weiss et al. | 424/423 |
| 2009/0155216 A1* | 6/2009 | Yamada et al. | 424/93.3 |

FOREIGN PATENT DOCUMENTS

| | | |
|---|---|---|
| EP | 1 303 586 A1 | 4/2003 |
| JP | 7-079772 A | 3/1995 |
| JP | 2003-304866 A | 10/2003 |
| WO | WO-98/41617 A1 | 9/1998 |
| WO | WO-02/00848 A1 | 1/2002 |
| WO | WO-03/087350 A1 | 10/2003 |
| WO | WO-2006/134921 A1 | 12/2006 |

OTHER PUBLICATIONS

Gestrelius et al., in vitro studies on periodontal ligament cells and enamel matrix derivativeJournal of Clinical Periodontology vol. 24, Issue 9, pp. 685-692, Sep. 1997.*
Diameter—Wikipedia, the free encyclopedia, pp. 1-3 last visited on Nov. 14, 2014.*
Daculsi et al ., Biphasic calcium phosphate concept applied to artificial bone, implant coating and injectable bone substitute. Biomaterials 191:473-1478;1998.*
Weiss Injectable Bone Substitute Using a Hydrophilic Polymer Bone vol. 25, No. 2, Supplement Aug. 1999:67S-70S.*
Minimum Essential Medium (MEM) Alpha Medium Corning Data shee 2015.*
Both et al A Rapid and Efficient Method for Expansion of Human Mesenchymal Stem Cells Tissue Engineering vol. 13, No. 1, 2007 pp. 3-9.*
Arweiler et al., Antibacterial effect of an enamel matrix protein derivative on in vivo dental biofilm vitality Clin Oral Invest (2002) 6:205-209.*
Corning (description of alpha Minimum Essential Medium (MEM) 2015.*
Ernst, M., et al.;"Osteoblastlike Cells in a Serum-free Methylcelluose Medium Form Colonies: Effects of Insulin and Insulinlike Growth Factor I"; Calcified Tissue International, 1987, vol. 40, pp. 27-34.
Daculsi, G. et al.;"Biphasic Calcium Phosphate/Hydrosoluble Polymer Composites: A New Concept for Bone and Dental Substitution Biomaterials"; Bone, vol. 25, No. 2, Aug. 1999, pp. 59S-61S.
Trojani, Christophe et al.; "Three-dimensional culture and differentiation of human osteogenic cells in an injectable hydroxypropylmethylcellulose hydrogel"; Biomaterials, 2005, vol. 26, pp. 5509-5517.
John, Annie et al.; "Tissue Engineered Bone and Adipose Tissue—An In Vitro Study"; Trends Biomater. *Artif.* Organs, 2002, vol. 16, No. 1, pp. 28-33.
Sanne, K et al.; "A rapid and efficient method for expansion of human mesenchymal stem"; National Library of Medicine (NLM), Tissue Engineering, Jan. 2007, vol. 13, No. 1, pp. 3-9, abstract only.
Cukierman, Edna, et al.; "Taking Cell-Matrix Adhesions to the Third Dimension"; Science, 2001, vol. 294, pp. 1708-1712.
Griffith, Linda, G., et al.; "Tissue Engineering—Current Challenges and Expanding Opportunities"; Science, 2002, vol. 295, pp. 1009-1014.
Schmeichel, Karen, L. et al.; "Modeling tissue-specific signaling and organ function in three dimensions"; Journal of Cell Science, 2003, vol. 116, pp. 2377-2388.

(Continued)

*Primary Examiner* — Maria G Leavitt
(74) *Attorney, Agent, or Firm* — Blank Rome LLP

(57) ABSTRACT

A method of culturing human or mammalian mesenchymal stem cells (MSC) or osteoblastic cells to form corresponding cell aggregates evenly distributed in the culturing medium having a reduced content of cells with fibroblast morphology comprises contacting MSC or OC with a water-soluble cellulose derivative over a period of from 1 day to one or two weeks. Also disclosed are a corresponding aggregates, a culture medium and a pharmaceutical composition, and uses of the aggregate, the culturing medium and the composition.

10 Claims, 5 Drawing Sheets

(56) References Cited

OTHER PUBLICATIONS

Yamada, Kenneth M., et al.; "Survival in three dimensions"; Nature, 2002, vol. 419, pp. 790-791.

Gumbiner, Barry M.; "Cell Adhesion: The Molecular Basis of Tissue Architecture and Morphogenesis"; Cell, 1996, vol. 84, pp. 345-357.

Ohlstein, Benjamin et al.:"The stem cell niche: theme and variations"; Current Opinion in Cell Biology, 2004, vol. 16, pp. 693-699.

Engler, Adam, J. et al.;"Matrix Elasticity Directs Stem Cell Lineage Specification"; Cell, 2006, vol. 126, pp. 677-689.

Grimandi, G., et al.:"In vitro evaluation of a new injectable calcium phosphate material"; J. Biomed Mater Res, 1998, vol. 39, pp. 660-666.

Lerouxel, Emmanuelle et al.; "Injectable calcium phosphate scaffold and bone marrow graft for bone reconstruction in irradiated areas: An experimental study in rats"; Biomaterials, 2006, vol. 27, pp. 4566-4572.

Vinatier C., et al.; "A silanized hydroxypropyl methylcellulose hydrogel for the three-dimensional culture of chondrocytes"; Biomaterials, 2005, vol. 26, pp. 6643-6651.

Vinatier, C. et al.;"Engineering cartilage with human nasal chondrocytes and a silanized hydroxypropyl methylcellulose hydrogel"; J. Biomed Mater Res. Part A. 80A, 2007, pp. 66-74.

Jamal, Hassan H. et al.; "CD44 Expression in Fetal Rat Bone: In Vivo and in Vitro Analysis"; Experimental Cell Research, 1996, vol. 223, pp. 467-477.

Termine, John D. et al.:"Osteonectin, A Bone-Specific Protein Linking Mineral to Collagen"; Cell, Oct. 1981, vol. 26, pp. 99-105.

International Search Report for PCT/SE2008/000307, dated Jul. 14, 2008.

Boix, D. et al.; "Immediate Implantation of Titanium Dental Implants Associated to an Injectable Bone Substitute Immediately After Tooth Extraction"; European Cells and Materials, vol. 1, Suppl.1, 2001, pp. 20-21.

Grimandi, G. et al.; "In vitro evaluation of a new injectable calcium phosphate material"; ©1998 John Wiley & Sons, Inc. pp. 660-666.

* cited by examiner

METHOD AND MEANS FOR CULTURING OSTEOBLASTIC CELLS

FIELD OF THE INVENTION

The present invention relates to a method of culturing human or mammalian mesenchymal stem cells and osteoblastic cells to form cell aggregates (clusters) distributed evenly in the culture medium. The present invention also relates to a corresponding means and its use, to carrier compositions for osteoblastic cells and to other aspects of so cultured aggregates of osteoblastic cells such as reparation of living fractured bone, bone tissue regeneration and implantation of medical devices into bone.

BACKGROUND OF THE INVENTION

Currently a number of studies emphasize the importance of developing culturing systems that mimic similar organization of cells similar to that appearing in intact tissue (Cukierman E et al., 2001; Griffith and Naughton, 2002; Schmeichel and Bissell, 2003). Such a culturing system is believed to create a more appropriate dynamic system for research and clinical approaches. An environment that encourages cell growth into a three dimensional (3D) structure (cell aggregates) without the requirement of other manipulation or serial culturing is not possible with standard culture plates. Cells cultured in such a medium might also induce changes in cell geometry necessary to favor proliferation responses. The maintenance of stem cells properties in culture and the generation of larger numbers of stem cells are essential criteria for their clinical application.

Hydrogels such as agarose, alginate, gelatin, fibrin, and others have been used in 3D osteoblast cell culturing, and in the in vivo delivery of such cells to implantation sites (Trojani C et al., 2005). These studies demonstrated good cell viability and opportunity for inducing cell differentiation in the hydrogel cell culture. However, mechanical damage to cells, possible hindrance of cell migration and, consequently, low integration percentage in the implantation site have to be taken into account when using gel-encapsulated cells for in vivo cell delivery applications.

It is evident from several studies that complex cell to cell and cell to extracellular matrix interactions are taking place in living tissue (Yamada and Clark, 2002; Gumbiner B M, 1996; Ohlstein B et al., 2004). Engler (2006) found that matrix stiffness can modify the direction of differentiation of human mesenchymal stem cells. They showed that soft substrates mimic the elasticity of brain tissue, whereas stiff substrates mimics the matrix of bone in governing the differentiation of stem cell. A major problem is to identify substrates that mirror the original three-dimensional cell organization in a given living tissue to allow the development an efficient in-vitro 3D cell culture system.

Hydroxypropyl-methyl cellulose (HPMC) has been employed in combination with biphasic calcium phosphates (BCP) to produce injectable bone substitute for cavity filling in bone repair (Grimandi G et al., 1998; Lerouxel E et al., 2006). Grimandi et al. demonstrated that a combination of HPMC and calcium phosphates is not toxic in vitro, and they observed inhibition of cell growth as they used the pre-incubated media extraction on HPMC and calcium phosphates to evaluate cell growth. Lerouxel (2006) used a injectable calcium phosphate scaffold (ICPS, consisting of a mixture of BCP calcium granules and a cellulosic polymer derivative) as a carrier for bone marrow graft to fill defect areas in an animal model for irradiated bone defect. They showed a significant increase in bone repair when using a mixture of bone marrow cells and ICPS to fill bone defects compared with grafting ICPS only.

Bone tissue regeneration in dental, plastic/reconstructive and orthopaedic applications aims at coping with different kinds of injuries by which bone tissue has been impaired. A graft material is placed in or on a graft site followed by covering the graft material and the site with a barrier. New bone growth is induced at the site by host resorption of the graft material. The graft material must be able to induce bone formation in the site. The barrier material should be biodegradable. Titanium and tantalum are biocompatible metals used as bone substitute and/or in bone replacement and/or for fixtures in implant and/or prosthetic surgery.

Dental implants fixed in a jaw are frequently used for teeth replacement after parodontitis or other causes of loss of teeth. For a successful fixation of a dental implant the jaw must contain a sufficient amount of bone material. Amelogenin (Emdogain®) is a matrix protein mixture used in the regeneration of lost attachment of teeth. The agent precipitates on the tooth root surface and induces stem cell colonization resulting in root attachment. Osteoporosis is a result of an imbalance between bone resorption and bone formation, in which osteclasts resorb bone tissue faster than it is formed by osteoblasts. Osteoporotic bones are more prone to fracture. Typical osteoporotic fractures occur in the vertebral column, the hip and the wrist.

A silanized hydroxypropyl methyl cellulose (Si-HPMC) has been used for 3D cell culture of human chondrocytes and human osteogenic cells. (Vinatier C et al., 2005; Vinatier C et al., 2007; Trojani C et al., 2005). The Si-HPMC scaffold is however not water-soluble and thus cannot be removed by rinsing the cultured osteogenic cells with aqueous media such as body fluids.

WO 98/041617 discloses an aqueous solution of hydroxypropyl-methyl cellulose (HPMC) for use as a medium to stimulate the growth of cultured pancreatic beta-cells. EP 1 303 586 A1 discloses an aqueous solution of HPMC as a DNA/RNA-embedding medium.

Collagen type I is the most abundant bone matrix protein. It constitutes ninety percent of the total organic matrix of mature bone cells, which is responsible for the strength of the tissue. Osteocalcin is a later marker for osteogenesis and is involved in matrix mineralization and its expression closely mirrors the course of mineralization. It has a regulatory role in balancing bone mineralization (Termine J D et al., 1981). CD44 is considered as a marker for osteocytes. Expression of the CD44 gene has been detected in all stages of osteoblastic cell differentiation. It has been suggested that CD 44 gene expression it might play a role in osteogenesis and in bone tissue organization (Jamal and Aubin, 1996).

JP 7079772 A discloses a cell culture liquid comprising a water soluble polymer such as methyl cellulose or carboxymethyl cellulose for use in the production of cell spheroids from human fibroblasts of a controlled size. The spheroids so produced are intended for in-vitro assessment of toxicity of drugs.

JP 2003304866 A1 discloses float-cultured cell aggregates of chondrocytes and normal bone cells in a container with non-adhesive walls.

Mesenchymal stem cells (multipotent stromal cells) are multipotent cells capable of differentiating into a variety of cell types, such as osteoblasts and chondrocytes. A problem in the culture of mesenchymal stem cells and osteoblasts are the low expansion levels obtained with cell culturing methods known in the art.

OBJECTS OF THE INVENTION

It is an object of the invention to provide a method of culturing human or mammalian mesenchymal stem cells to osteoblastic cells, in particular osteoblastic cells in form of evenly distributed 3-D cell aggregates.

It is another object of the invention to provide a method of culturing human or mammalian mesenchymal stem cells to osteoblastic cells or of culturing human or mammalian osteoblastic cells exhibiting a reduced level of osteogenic gene expression during their culture.

Still another object of the invention is to provide an mesenchymal stem cell or osteoblastic cell aggregate having a reduced content of cells with fibroblast morphology.

A further object of the invention is to provide a medium for culturing human or mammalian mesenchymal stem cells or osteoblastic cells including cells to make them form cell aggregates, in particular cell aggregates having a reduced content of cells with fibroblast morphology.

An additional object of the invention is to provide the use of a culture medium for such cells in therapy.

Other objects of the invention will become evident from the following summary of the invention, the description of preferred embodiments thereof, and the appended claims.

SUMMARY OF THE INVENTION

The present invention is based on the insight that culturing mammalian or human (primary) mesenchymal stem cells and osteoblastic cells in the presence of a water-soluble cellulose derivative results in enhanced expansion and the formation of aggregates or clusters of mesenchytmal stem cells or of osteoblastic cells evenly distributed in the culture medium. In contrast, culturing such cells in the absence of a water-soluble cellulose derivative under otherwise identical conditions results in the cells adhering to surfaces of the culturing equipment as a monolayer preserving their fibroblast-like morphology, no clusters or aggregates being formed. In particular, the present invention is based on the insight that culturing human or mammalian mesenchymal stem cells or osteoblastic cells in the presence of a water soluble cellulose derivative over a restricted period of time, such as over two weeks or less, in particular over a time of one week or less, allows to obtain aggregates or clusters of osteoblastic cells having a reduced content of fibroblasts. In addition expansion of such cells in the presence of a water soluble cellulose derivative in a culture medium containing a water-soluble cellulose derivative proceeds at an substantially increased expansion rate in comparison with the expansion rate in absence of the cellulose derivative. The cell aggregates or clusters of the invention are observed in the culture medium within 24 hours from start. In this application a "reduced content of cells with a fibroblast morphology" in an aggregate or cluster of osteoblastic cells has the meaning of a content reduced in respect of the content obtained in a corresponding culture in absence of the water-soluble cellulose derivative. A reduced content of cells with fibroblast morphology is, for instance, a content reduced by 20% or more, more preferred by 50% or more, most preferred by 70% or more. A reduced content of cells with fibroblast is believed to be advantageous, i.a, in delaying the transformation of osteoblastic cell aggregates to osteocyte aggregates, that is, the mineralization of the osteoblastic cell aggregates in vitro and in vivo in the presence of mineral sources of appropriate kind. Such a reduced content also allows to obtain such cell aggregates faster and in substantially greater amounts than by known culturing processes. In experiments with mouse MC3T3-L1 (proto)osteoblastic cells and (primary) human mesenchymal stem cells, it was observed that their culture in presence of the water-soluble cellulose derivative of the invention enhances cell proliferation two-fold or even more; concomitantly the expression of osteoblastic cell markers indicative of differentiation towards mature osteoblasts and calcium content indicative of cell death was observed to be reduced in the respective cell culture medium. The physical nature of the aggregates or clusters of the invention makes them suitable for injection into sites of bone defect in a living bone, for drug delivery, and for implant integration.

In accordance with the present invention is provided a method of the aforementioned kind comprising contacting the mesenchymal stem cells or osteoblastic cells in vitro or in vivo with a water-soluble cellulose derivative. It is preferred for the water-soluble cellulose derivative to comprise cell growth promoting or sustaining agent selected from salts comprising essential elements, mono- and disaccharides, amino acids, peptides, proteins, and hormones. The method of the invention allows in particular to expand mesenchymal stem cells and osteoblastic cells easily and in a short time while preserving their intrinsic phenotype properties. The expanded cells can be used for filling defect sites, for drug delivery, and for integrating implants into bone tissue.

Cellulose derivatives of the invention are alkylated, hydroxy-alkylated, and alkylated/hydroxy-alkylated celluloses. Particularly preferred is hydroxyethyl cellulose, hydroxypropyl cellulose, methyl cellulose, ethyl cellulose, hydroxyethyl-methyl cellulose, hydroxyethyl-ethyl cellulose, hydroxypropyl-methyl cellulose. Most preferred is hydroxypropyl-methyl cellulose (HPMC). The use of silated cellulose derivatives is not comprised by the invention.

The term cellulose derivative as used herein excludes derivatives of cellulose obtained by substantial degradation of the cellulose chains to fragments having an average molecular weight of 2,000 Da or less. In this application "water soluble" refers to water or to aqueous media of a physiological pH, in particular a pH of about 7-8. The cellulose derivative of the invention should possess a gel-forming capability similar to that of a pharmaceutical grade hydroxymethyl propyl cellulose (HPMC) produced by the Dow Chemical Company, West Point Pa., U.S.A and marketed under the trade name METHOCEL™ E4M. A 2% solution of this polymer in water has a viscosity of from 3000 to 5600 mPa·s. In the invention the amount of cellulose derivative is adapted to the method of mesenchymal stem cell or osteoblastic cell culture so as keep the viscosity of the culture medium at an acceptable level. A high viscosity of the culture medium should however be avoided since it does negatively affect the cell growth rate. A viscosity of an aqueous solution of the water-soluble cellulose derivative of the invention corresponding to that of an aqueous solution of METHOCEL™ E4M of from 0.3% by weight to 1.0% is preferred. In all aspects of the invention the water-soluble cellulose derivative is used in a cell growth promoting amount. A cell growth promoting amount is an amount that increases the rate of cell growth in a culture medium in respect of the cell growth rate in a corresponding culture medium lacking the water-soluble cellulose derivative of the invention.

Thus, according to the present invention is provided a method of in-vitro culturing human or mammalian mesenchymal stem cells or osteoblastic cells to form corresponding cell aggregates evenly distributed in the culture medium comprising contacting, over a period from 1 day to three days or one or even two weeks, the mesenchymal stem cells or osteoblastic cells with a culture medium comprising a of a water-soluble cellulose derivative selected from alkylated, hydroxy-alkylated, and alkylated/hydroxy-alkylated cellulose or a mixture thereof, and cell growth promoting or sustaining agent selected from salts comprising essential elements, mono- and disaccharides, amino acids, peptides, proteins, and hormones, wherein the cell aggregates have a reduced content of cells with fibroblast morphology, in particular one reduced by 20% or more, more preferred by 50% or more, most preferred by 70% or more, in respect of a corresponding content obtained in the absence of the water-soluble cellulose derivative.

According to a first preferred aspect of the invention is provided a cell culture medium for in-vitro or in-vivo culturing of human or mammalian mesenchymal stem cells or osteoblastic cells, comprising (a) water-soluble cellulose derivative of the invention (b) one r more cell growth promoting or sustaining agents selected from the group consisting of salts of essential elements, mono- and disaccharides, amino acids, peptides, proteins, and hormones, (c) optionally a pharmaceutical, in particular an antibiotic, (d) a source of calcium and a source of phosphate. In the cell culture medium of the invention the source of calcium preferably comprises a calcium salt, in particular a calcium salt selected from the group consisting of calcium monophosphate, calcium hydrogen phosphate, calcium pyrophosphate, calcium citrate. In the cell culture medium of the invention the source of phosphorous preferably comprises a phosphate, in particular a phosphate selected from calcium mono-phosphate, calcium hydrogen phosphate, calcium pyrophosphate. According to the invention the cell culture medium may additionally or independently comprise substantially water-insoluble particulate material selected from the group consisting of calcium hydroxy apatite, a substantially water-insoluble calcium phosphate, and bone meal. Ninety-five percent of the particles of the particulate material advantageously have a diameter of from 2 µm to 50 µm. The culture medium of the invention may furthermore comprise a proteinaceous enamel matrix derivative for periodontal tissue regeneration, in particular amelogenin.

Other than for in-vitro culturing of human or mammalian mesenchymal stem cells and osteoblastic cells the culture medium of the invention has a number of preferred uses, such as a glue for gluing fractured living bone and for gluing fixation of a biocompatible material to living bone. Any biocompatible material that can be wetted by the culture medium of the invention can be used; preferred materials are titanium, hafnium and ceramic materials as well as polymer materials such as polyurethane, polyurethane urea), polylactate, polyglycolate, poly(lactate, glycolate).

According to a second preferred aspect of the invention is disclosed a pharmaceutical composition for use in osteoporosis treatment, comprising mesenchymal stem cell aggregates and osteoblastic cell aggregates cultured for a time of one days to one week or two weeks, in the presence of a gel of a water-soluble cellulose derivative selected from alkylated, hydroxy-alkylated, or alkylated/hydroxy-alkylated cellulose or mixtures thereof, in particular HPMC, which cell aggregates have a reduced content of cells with fibroblast morphology. The composition optionally comprises one or several agents selected from the group consisting of saline or other osmotic pressure controlling agent, cell growth promoting or sustaining agent selected from salts comprising essential elements, mono- and disaccharides, amino acids, peptides, proteins, and hormones dissolved in the gel. The reduced content of cells with fibroblast morphology is one reduced by 20% or more, more preferred by 50% or more, most preferred by 70% or more, in respect of a corresponding content obtained in the absence of the water-soluble cellulose derivative. Preferred uses of the pharmaceutical composition of the invention comprise plastic and reconstructive surgery.

According to a third preferred aspect of the invention is disclosed a human or mammalian mesenchymal cell aggregate or osteoblastic cell aggregate having a reduced ratio of cells with fibroblast morphology, in particular one reduced by 20% or more, more preferred by 50% or more, most preferred by 70% or more, in respect of a corresponding content obtained in the absence of the water-soluble cellulose derivative, obtainable by in-vitro culture over a time of from one day to one week or one day to two weeks, of human or mammalian mesenchymal stem cells or osteoblastic cells in an aqueous medium comprising a water-soluble cellulose derivative of the invention and one or more of the group consisting of saline or other osmotic pressure controlling agent, and cell growth promoting or sustaining agent selected from salts comprising essential elements, mono- and disaccharides, amino acids, peptides, proteins, and hormones dissolved in the gel. A preferred use of the osteoblastic cell aggregate of the invention is in bone regeneration.

According to a fourth preferred aspect of the invention is disclosed the use of a the cell culture medium comprising a water-soluble cellulose derivative for in-vitro or in-vivo culturing of human or mammalian mesenchymal stem cells or osteoblastic cells to form corresponding cell aggregates having a reduced content of cells with fibroblast morphology, in particular one reduced by 20% or more, more preferred by 50% or more, most preferred by 70% or more, in respect of a corresponding content obtained in the absence of the water-soluble cellulose derivative. The human or mammalian mesenchymal cell aggregates or osteoblastic cell aggregates of the invention are formed during a culture period extending from 1 day to one or two weeks. The culture medium can additionally comprise cell growth promoting or sustaining agents selected from salts comprising essential elements, mono- and disaccharides, amino acids, peptides, proteins, and hormones, and optionally comprises a pharmaceutical, in particular an antibiotic. A preferred use is in dental bone tissue regeneration; in such case the culture medium can comprise a proteinaceous enamel matrix derivative for periodontal tissue regeneration, in particular amelogenin. Another preferred use is in orthopaedic bone tissue regeneration. Advantageously the culture medium can comprises a source of calcium and a source of phosphate. It is preferred for the source of calcium to comprise a calcium salt, in particular a calcium salt selected from the group consisting of calcium mono-phosphate, calcium hydrogen phosphate, calcium pyrophosphate, calcium citrate. A preferred source of phosphorous is a phosphate, in particular a phosphate selected from calcium mono-phosphate, calcium hydrogen phosphate, calcium pyrophosphate. The culture medium may additionally comprise substantially water-insoluble particulate material selected from the group consisting of calcium hydroxy apatite, calcium phosphate, and bone meal, with 95% by weight or more of the particles having a diameter of is from 2 µm to 50 µm.

According to a fifth preferred aspect of the invention is disclosed a medical device for anchoring in bone, comprising a metallic anchoring surface area covered with a gel or a dried gel of the water-soluble cellulose derivative of the invention or with the culture medium of the invention or with the pharmaceutical composition of the invention. The metal of the device is preferably selected from titanium, tantalum and their alloys. The anchoring surface can be the surface of a plate, thread, screw, staple or other osseofixation element.

According to a sixth preferred aspect of the invention is disclosed the use of a water-soluble cellulose derivative in the delivery of human mesenchymal stem cells (MSC) to a patient. A composition of human mesenchymal stem cells (MSC) for delivery to a patient comprises a pharmaceutically acceptable aqueous carrier and a water-soluble cellulose derivative of the invention in a preferred amount of from 0.2 percent by weight to 5 percent by weight, in particular from 0.2 percent by weight to 2 percent by weight, of the composition. The mesenchymal stem cells are preferably autologous cells. A method of regeneration of bone in a patient having a bone defect comprises procuring human mesenchymal stem cells (MSC) from the patient, expanding them in a culture medium comprising the water-soluble cellulose derivative of the invention, harvesting the expanded cells, injecting them into the bone defect of the patient. The mesenchymal stem cells are injected into the patient suspended in an aqueous injection medium comprising the water-soluble cellulose derivative of the invention.

The invention will now be explained in greater detail by reference to preferred but not limiting embodiments illustrated in a number of figures.

SHORT DESCRIPTION OF THE FIGURES

Figure 4:
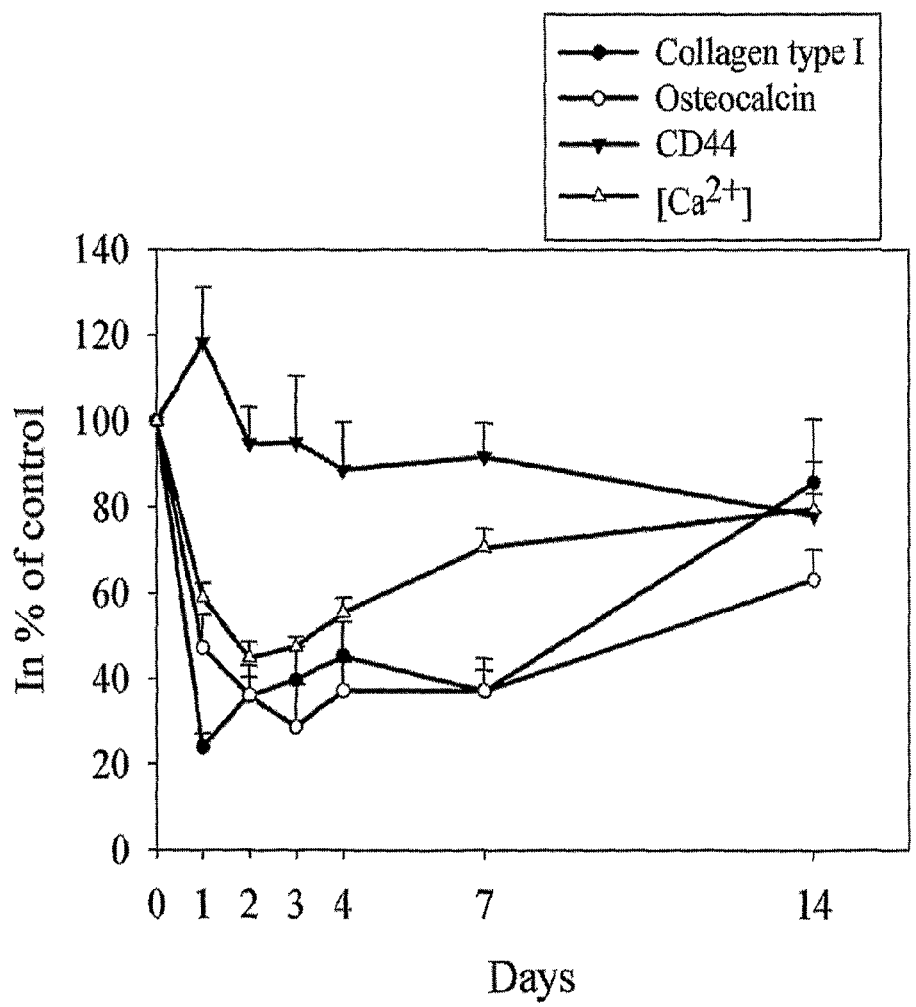

FIG. 4 is a diagram showing the expression of collagen type I mRNA, osteocalcin mRNA, CD44 mRNA as well as $Ca^{2+}$ concentration in a MC3T3-E1 cell culture in a medium comprising HPMC gel of the invention as a percentage of the corresponding expression or concentration in a control medium. The expression was calculated relative to the expression of two housekeeping genes (RPII and GAPDH) in each individual sample. The results are calculated in % of control at each time point, and the data presented as mean±SEM from five experiments.

DESCRIPTION OF PREFERRED EMBODIMENTS OF THE INVENTION

Cell Cultures.

The mouse osteoblastic cell line MC3T3-E1 (DSMZ, ACC210, Braunschweig, Germany) was cultured in alpha-MEM (PAA Laboratories GmbH, Austria) supplemented with 20% fetal calf serum (PAA Laboratories GmbH, Austria) and 1% penicillin/streptomycin (100 μg/mL penicillin and 100 μg/mL streptomycin). The cells were kept in an incubator at 37° C. in a humidified atmosphere (95% air and 5% $CO_2$). The cells were sub-cultured twice a week at 80%-90% confluent using 0.25% trypsin containing 1 mM EDTA. Human mesenchymal stem cells (MSC; Cambrex Bio Science Walkersville Inc., MD, USA) were cultured in MSC basal medium (Cambrex Bio Science Walkersville Inc., MD, USA) supplemented with 200 mM L-glutamine (Cambrex Bio Science Walkersville Inc., MD, USA) and 1% penicillin/streptomycin (Cambrex Bio Science Walkersville Inc., MD, USA). The cells were sub-cultured at 80%-90% confluent using 0.25% trypsin containing 1 mM EDTA.

Experimental Design.

The cells were cultured in their respective culturing media, supplemented alpha-MEM and MSC basal medium, respectively, as described above, in culture inserts in 24-well cell culture plates. Two types of culture inserts (Millipore Corp. Ireland) were tested in parallel; PCF (polycarbonate) and CM (hydrophilic poly(tetrafluoro-ethylene) with 0.4 μm pore size. The cells were suspended in a preferred embodiment of the gelatinous medium of the invention (g/L: 12.0, HPMC (METHOCEL™ E4M, Medical Grade; Dow Chemical Company); KCl, 0.45; NaCl, 6.0; $KH_2PO_4$, 0.45; $Na_2HPO_4.2H_2O$, 15.2; $NaH_2PO_4.H_2O$, 2.2; water to 1 L; 1 L; η=125 (mPa·s)) or in the ordinary culture medium only, respectively, in two compartments of the cell culture plate, to a final concentration of $0.5 \times 10^6$ cells/mL and gently mixed to make a homogeneous suspension. The culture inserts containing 500 μl cell suspension were placed in the wells of the 24-well plate already containing 500 μl of cell culture medium. The medium was changed every other day. The plates were placed in an incubator at 37° C. in a humidified atmosphere (95% air and 5% $CO_2$) for up to 14 days.

Morphology.

To evaluate the morphology of the cells in the gelatinous cell medium of the invention, all cultures were examined daily using an Olympus inverted light microscope (Olympus Deutschland GmbH, Hamburg, Germany).

Cell Proliferation Assay.

Cell proliferation rate was determined by [$^3$H]-thymidine incorporation after 24, 48 and 72 hours of cell culturing. MC3T3-E1 cells were cultured at concentration of $0.5 \times 10^6$ cells/mL with and without the gelatinous medium of the invention, in both types of cell culture inserts. Cells were exposed to 1 μCi/well [$^3$H]-thymidine for 12 hours prior to harvesting of the cells. Cells of each culture insert were transferred to 1.5 mL tubes. Both cell culture inserts and cells in the tubes were washed twice with ice-cold 1×PBS and twice with ice-cold 5% trichloroacetic acid to remove unincorporated [$^3$H]-thymidine. To ensure against losing cells during the washing steps, washing solution discarded from the inserts were collected in their respective tube material and centrifuged for 3 min. at 13,000×g along with the washed cells. The cells in the tubes and potential cells left in culture inserts were solubilized in 500 μl 1M NaOH. 400 μl of the solubilized cell solution were transferred to 8 mL of Insta-gel II Plus liquid scintillation fluid and measured for 3 min. in a Packard liquid scintillation counter (Packard, Zurich, Switzerland). To ensure that any observed effects of HPMC gel were not due to serum dilution or variations in serum concentration, the effect of serum dilution in the HPMC gel culture on cell proliferation was investigated at various HPMC gel to serum ratios. Variations in serum concentration were not found to have a significant effect on cell proliferation in any of the cell types studied.

Cell Viability.

To characterize the viability status of the culture in the gelatinous medium of the invention, the lactate dehydrogenase (LDH) release of the MC3T3-E1 cell cultures into the supernatant was measured after 1, 2, 4, 7 and 14 days. The LDH release was measured for cells with and without (control) HPMC and for both above-mentioned culture inserts. Cell cultures were started at a concentration of $0.5 \times 10^6$ cells/mL in the inserts and on the plastic plates. LDH activity was measured using the Cytotoxicity Detection Kit (LDH) (Boehringer, Mannheim, Germany). According to the protocol, 50 µl cell sample was placed in a 96-well plate together with 50 µl kit mixture (catalyst and colour solution), placed in the dark for 30 min., thereafter the absorbance was read on an ELISA reader at 450 nm. Low and high controls were included in all measurements. The LDH activity in fresh culture medium was measured as a low control (or as background absorbance). Maximum release amount of LDH (high control) was determined by lysing cells on a plastic plate with Triton X-100. The percentage of LDH activity was calculated using following equation:

LDH activity (%)=exp. Value–low control/high control–low control×100 mRNA Isolation.

All cell culture media from each well was carefully collected and stored at −20° C. Cells were lysed in a lysis/binding buffer (100 mM Tris-HCl, pH 8.0, 500 mM LiCl, 10 mM EDTA, pH 8.0, 0.5 mM dithiothreitol (DTT), and 1% sodium dodecyl sulfate (SDS)). mRNA was isolated using magnetic beads, Dynabeads® Oligo(dT)$_{25}$ as described by the manufacturer (Dynal AS, Oslo, Norway). Beads containing mRNA were re-suspended in 10 mM Tris-HCl, pH 8.0, and stored at −70° C. until use. 1 µL of the mRNA-containing solution was applied directly to obtain a first-strand complementary DNA (cDNA) using the iScript cDNA Synthesis Kit which contains both Oligo(dT)$_{25}$ and random hexamer primers (Bio-Rad, Hercules, Calif., USA).

Real-time PCR. Reactions were performed and monitored using iCycler iQ (Bio-Rad, Hercules, Calif., USA). The 2×iQ SYBR Green Supermix was based on iTaq DNA polymerase (Bio-Rad, Hercules, Calif., USA). The amplification program consisted of a pre-incubation step for denaturation of the template cDNA (3 min., 95° C.), followed by 50 cycles consisting of a denaturation step (15 s, 95° C.), an annealing step (15 s, 60° C.) and an extension step (30 s, 72° C.). After each cycle, fluorescence was measured at 72° C. A negative control without the cDNA template was run in each assay. Samples were run in duplicate. To allow relative quantification after the PCR, standard curves were constructed from the standard reactions for each target and housekeeping genes by plotting Ct values, i.e. the cycle number at which the fluorescence signal exceeds background, versus log cDNA dilution. The Ct readings for each of the unknown samples were then used to calculate the amount of either the target or housekeeping relative to the standard. mRNA levels were calculated as the ratio of relative concentration for the target genes relative to that for the mean between housekeeping genes. cDNA was analyzed for the relative transcriptional expression of type I collagen, osteocalcin, alkaline phosphatase, CD44, bone sialoprotein, Osterix. The housekeeping gene GAPDH and oligonucleotide primer sequences used for the real-time RT-PCR and the specific parameters are shown in the Table. Real-time efficiencies were calculated from the given slopes in the iCycler software using serial dilutions, showing all the investigated transcripts high real-time PCR efficiency rates, and high linearity (r>0.99) when different concentrations were used. PCR products were subjected to a melting curve analysis on the iCycler and subsequently 2% agarose/tris-acetic acid-EDTA (TAE) gel electrophoresis to confirm amplification specificity, $T_m$ and product size, respectively (Table).

TABLE

Primers used in real-time PCR quantification

| Gene | Primer sequence* | Species | Amplicon size (bp) |
| --- | --- | --- | --- |
| Alkaline phosphatase | S 5'- AACCCAGACACAAGCATTCC -3'<br>A 5'- GAGAGCGAAGGGTCAGTCAG -3' | Mouse | 151 |
| Bone sialoprotein | S 5'- GAAAATGGAGACGGCGATAG -3'<br>A 5'- ACCCGAGAGTGTGGAAAGTG -3' | Mouse | 141 |
| CD44 | S 5'- CTTCCATCTTGACCCGTTGT -3'<br>A 5'- ACAGTGCTCCTGTCCCTGAT -3' | Mouse | 175 |
| Collagen-I | S 5'- AGAGCATGACCGATGGATTC -3'<br>A 5'- CGTTCTTGAGGTTGCCAGTC -3' | Mouse | 177 |
| Osteocalcin | S 5'- CCGGGAGCAGTGTGAGCTTA -3'<br>A 5'- TAGATGCGTTTGTAGGCGGTC -3' | Mouse | 80 |
| Osterix | S 5'- ACTGGCTAGGTGGTGGTCAG -3'<br>A 5'- GGTAGGGAGCTGGGTTAAGG -3 | Mouse | 135 |
| GAPDH | S 5'- ACCCAGAAGACTGTGGATGG -3'<br>A 5'- CACATTGGGGGTAGGAACAC -3' | Mouse | 171 |

*Oligonucleotide sequences of sense (S) and antisense (A) primers used in the real-time PCR of target and housekeeping gene.

Statistical Analysis.

Figure 1:
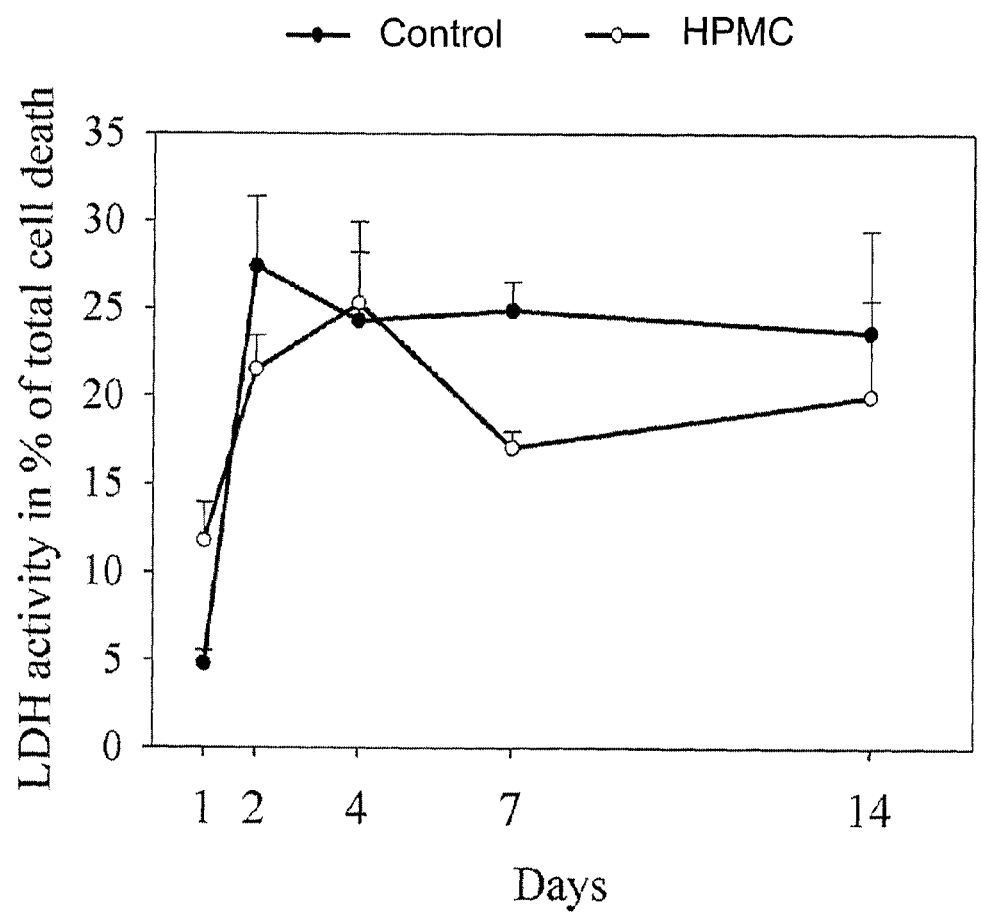
FIG. 1 is a diagram showing the LDH release in a cell culture of the invention and control culture (MC3T3-E1 cells cultured at $0.5 \times 10^6$ cells/ml in presence of HPMC and in absence of HPMC. Data are means±SEM from four individual experiments.

Statistical analysis was performed with a one-way analysis of variance (ANOVA) for repeated measurements. The significance of difference was assessed by either the Student's t-test or the Mann-Whitney U test. Significance was set at P<0.05. Cell cytotoxicity effect. Similar values were obtained for the LDH activity in PCF and CM culture inserts for MC3T3-E1 cells (FIG. 1). An increase in LDH activity was observed for cell cultures in the gelatinous medium of the invention. However, it was only significantly higher at day 7 for cell cultures with the gelatinous medium of the invention in comparison with the control. The rate of LDH activity for cell cultures with the gelatinous medium of the invention and control increased up to day 4 in the cultures and from day 5 and onwards the rate become constant throughout the remaining culture period.

Cell Morphology.

Figure 2B:
FIGS. 2A and 2B are a phase contrast microscopy photographs of MC3T3-L1 cells after 3 days in culture: (A) in the presence of HPMC, (B) control.
Figure 2A:
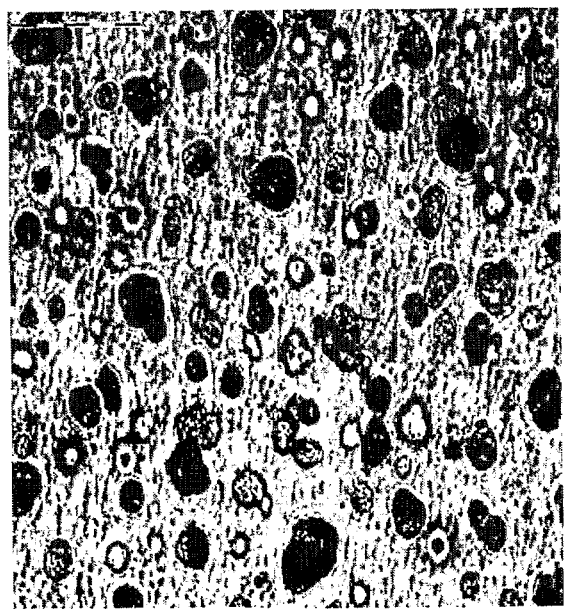

The CM inserts allow visualization of cells using an inverted W microscope. Both MCS and MC3T3-E1 cells cultured in the gelatinous medium of the invention showed a multi-cellular aggregate morphology within 24 hours of cell growth (FIG. 2A). The cells had a round morphology and the aggregates were evenly distributed throughout the gel. The cells in the cell culture in absence of the gelatinous medium of the invention maintained their fibroblast-like morphology and were not distributed evenly on the culture insert surface (FIG. 2B). They formed an irregular netting structure.

Cell Proliferation.

Figure 3A:
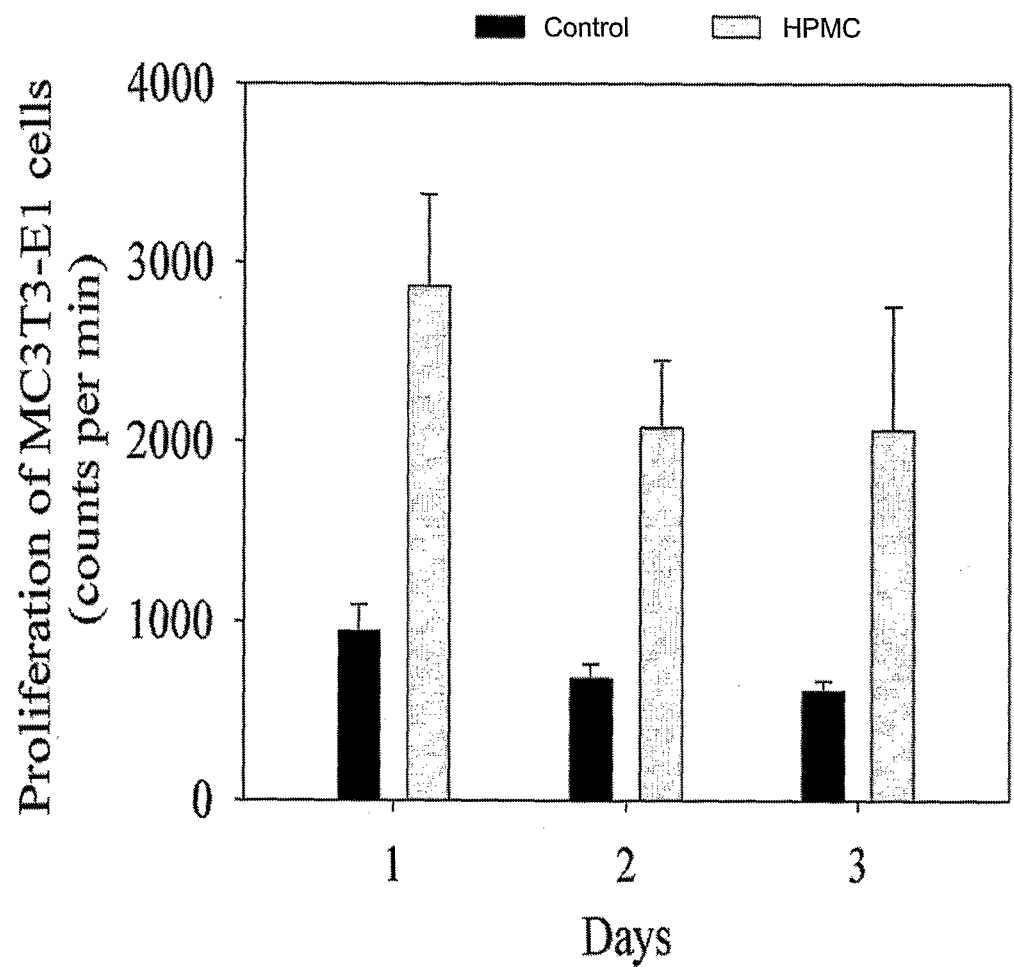
FIG. 3a is a diagram showing the proliferation of MC3T3-E1 cells in the presence of HPMC and in a control. The data are means±SEM from 4 experiments.
Figure 3B:
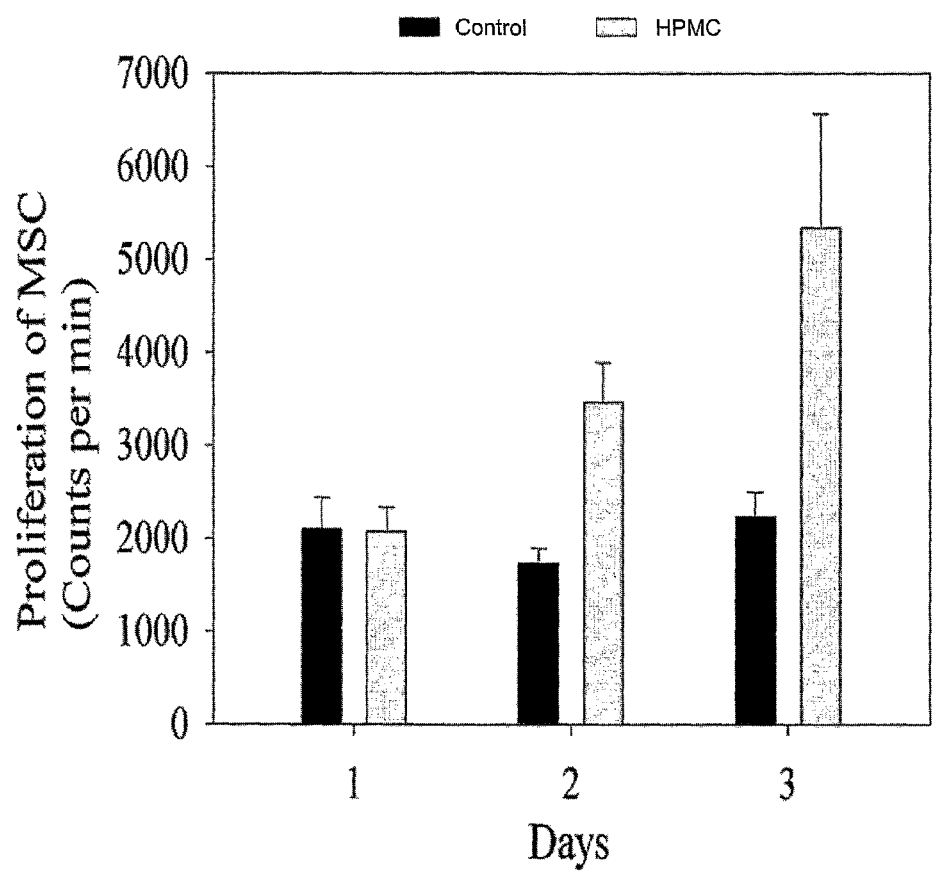
FIG. 3b is a diagram showing the proliferation of MSC cells in the presence of HPMC and in a control. The data are means±SEM from 4 experiments.

The number of MC3T3-L1 cells (FIG. 3A) and primary human MSCs (FIG. 3B) was significantly higher when cultured in HPMC gel compared to control. A 3-fold enhancement was observed at day 1 (P=0.029), a 5-fold enhancement at day 2 and day 3 (P=0.011 and P=0.029, respectively) of MC3T3-L1 cells, and a 2-fold increase at day 2 and 3 (P=0.007 and P=0.039, respectively) of MSCs. Cell proliferation was also more than 2-fold increased in HPMC gel in both MC3T3-E1 cells and MSCs when assayed for a possible serum dilution effect (data not shown).

Expression of Osteocalcin and Collagen Type 1 Markers.

mRNA expression of both osteocalcin and collagen type 1 was significantly reduced in MC3T3-E1 cells cultured in HPMC gel of the invention. In the presence of HPMC, as evident from FIG. 4, mRNA expression of osteocalcin and collagen type 1 was at a significantly reduced level over a culture period of 14 days, most particularly over a culture period of 7 days (P≤0.001 and P≤0.014, respectively). Also, collagen type 1 expression was at a significantly reduced level (P≤0.014). Except for at day 1 expression of CD44 was however not significantly affected. Calcium concentration was also significantly reduced during both culture periods (P≤0.002). mRNA expression of alkaline phosphatase (ALP), bone sialoprotein (BSP) and Osterix were close to detection limits or below in the cells cultured in the HPMC gel of the invention (data not shown).

Cell Proliferation.

For MC3T3-EI cells, with PCF and CM culture inserts, proliferation showed a comparable pattern with both cell culture inserts. There was significantly higher cell proliferation at all times for cell cultures with the gelatinous medium of the invention than for the control. There was a 5-fold increase in cell growth with the gelatinous medium of the invention at day 2 (P=0.011) and day 4 (P=0.029) compared to the control. Cell growth increased 3-fold at day 1 and was significantly higher (P=0.029). However, [$^3$H]-thymidine incorporation rate decreased during the three day experiment period. Cell proliferation for human mesenchymal stem cells was significantly increased in the gelatinous medium of the invention. There was more than a 2-fold increase at day 2 (P=0.007) and day 3 (P=0.039) in the gelatinous medium of the invention compared to the control. There was an identical rate of radioactive [$^3$H]-thymidine incorporated at 24 hours.

Gene Expression of Osteoblastic Marker.

The temporal expression of collagen type I, osteocalcin and CD44 to evaluate osteoblastic phenotypic properties of MC3T3-E1 were studied. The gene expression results were similar within both cell culture inserts. In general, the expression levels of collagen type I, osteocalcin and CD44 were lower in the cell cultures in the gelatinous medium of the invention compared to the control. The expression of collagen type I was increased 5-fold in the cell cultures in the gelatinous medium of the invention and more than 2-fold in the control. The collagen type I expression was significantly lower at day 1 (n=4, P=0.035) and day 4 (n=4, P=0.029) in the cell cultures in the gelatinous medium of the invention. No significant difference was observed for the CD44 gene expression level at any point in time during culture. However, the expression level was more than 5-fold increased in the control and 1.4-fold in the cell cultures in the gelatinous medium of the invention during the 14 days of culture. The osteocalcin gene expression was significantly lower in the cell cultures in the gelatinous medium of the invention compared to control (n=4, P=0.001) at day 7. The expression profile showed a 5-fold increase in the control and a 3-fold increase in the cell cultures in the gelatinous medium of the invention with time in culture. The expression of alkaline phosphates, bone sialoprotein and Osterix genes was negative or at negligible levels in both cell culture inserts in the gelatinous medium of the invention and in the CM inserts without the gelatinous medium of the invention. However, they were detected in low levels in the PCF culture insert without the gelatinous medium of the invention, which increased with culturing time. The expressions of alkaline phosphatase, bone sialoprotein and Osterix genes on the plastic culture plates showed increasing levels with increasing culturing time.

[Ca$^{2+}$] Measurements.

After harvesting the samples were lyophilized, homogenized in 3% HCl, and shaken for 24 h at room temperature. Calcium content was determined by atomic absorption spectroscopy (AAnalyst 400, PerkinElmer Instruments, Shelton, USA) in an air-acetylene flame. The interference with phosphate was suppressed by addition of 0.5% lanthanum to the standards and samples prior to measurements.

REFERENCES

1. Cukierman E et al. Science 294 (2002) 1708-1712.
2. Griffith L G and G Naughton, Science 295 (2002) 1009-1014.
3. Schmeichel K L and M J Bissell, J. Cell Sci. 116 (2003) 2377-2388.
4. Trojani C et al., Biomaterials 26 (2005) 5509-5517.
5. Yamada K M and K Clark, Nature 419 (2002) 790-791.
6. Gumbiner B M, Cell 84 (1996) 345-357.
7. Ohlstein B et al., Curr. Opin. Cell Biol. 16 (2004) 693-699.
8. Engler A J et al., Cell 126 (2006) 677-689.
9. Grimandi G et al., J. Biomed. Mater. Res. 39 (1998) 660-666.
10. Lerouxel E et al., Biomaterials 27 (2006) 4566-4572.
11. Vinatier C et al., Biomaterials 26 (2005) 6643-6651.

12. Vinatier C et al., J. Biomed. Mater. Res. Part A. 80A (2007) 66-74.
13. Jamal H H and J E Aubin, Exp. Cell Res. 223 (1996) 467-477.

The invention claimed is:

1. A culture medium for culturing of mammalian mesenchymal stem cells or osteoblastic cells consisting essentially of (a) a water-soluble cellulose derivative selected from the group consisting of hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose, (b) at least one cell growth promoting or sustaining agent, (c) water, (d) optionally a pharmaceutical, (e) a source of calcium and a source of phosphate, (f) optionally a water-insoluble particulate material, and (g) optionally a proteinaceous enamel matrix derivative for periodontal tissue regeneration.

2. The culture medium of claim 1, wherein the source of calcium comprises a calcium salt, and the source of phosphorous comprises a phosphate.

3. The culture medium of claim 2, wherein the source of calcium is selected from the group consisting of calcium mono-phosphate, calcium hydrogen phosphate, calcium pyrophosphate, and calcium citrate, and the source of phosphorous is selected from calcium monophosphate, calcium hydrogen phosphate, and calcium pyrophosphate.

4. The culture medium of claim 1 wherein the source of calcium is a water-insoluble particulate material selected from the group consisting of calcium hydroxy apatite, a water-insoluble calcium phosphate, and bone meal.

5. The culture medium of claim 4, wherein the water-insoluble particulate matter has a diameter, and the diameter of 95% by weight or more of the particulate material is from 2 µm to 50 µm.

6. The culture medium of claim 1, wherein the proteinaceous enamel matrix derivative for periodontal tissue regeneration is present.

7. A culture medium for culturing of mammalian mesenchymal stem cells or osteoblastic cells consisting (a) a water-soluble cellulose derivative selected from the group consisting of hydroxyethyl cellulose, hydroxypropyl cellulose, methyl cellulose, ethyl cellulose, hydroxyethyl-methyl cellulose, hydroxyethyl-ethyl cellulose, and hydroxypropyl-methyl cellulose, (b) at least one cell growth promoting or sustaining agent, (c) optionally a pharmaceutical, and (d) a source of calcium and a source of phosphate, (e) optionally a water-insoluble particulate material, and (f) optionally a proteinaceous enamel matrix derivative for periodontal tissue regeneration.

8. The culture medium of claim 7, wherein the source of calcium is a calcium salt, and the source of phosphorous is a phosphate.

9. The culture medium of claim 8, wherein the source of calcium is selected from the group consisting of calcium mono-phosphate, calcium hydrogen phosphate, calcium pyrophosphate, and calcium citrate, and the source of phosphorous is selected from calcium monophosphate, calcium hydrogen phosphate, and calcium pyrophosphate.

10. The culture medium of claim 7, wherein the proteinaceous enamel matrix derivative for periodontal tissue regeneration is present.

* * * * *